United States Patent [19]

Miyawaki et al.

[11] Patent Number: 4,703,760

[45] Date of Patent: Nov. 3, 1987

[54] ELECTRONIC BLOOD PRESSURE MEASURING DEVICE

[75] Inventors: Yoshinori Miyawaki, Yawata; Satoshi Ueno; Satoshi Egawa, both of Kyoto; Osamu Shirasaki, Amagasaki, all of Japan

[73] Assignee: Omron Tateisi Electronics Co., Kyoto, Japan

[21] Appl. No.: 839,580

[22] Filed: Mar. 14, 1986

[30] Foreign Application Priority Data

Mar. 15, 1985 [JP] Japan .................................. 60-52902
Mar. 22, 1985 [JP] Japan .................................. 60-59297

[51] Int. Cl.[4] .............................................. A61B 5/02
[52] U.S. Cl. ...................................... 128/681; 364/417
[58] Field of Search ........................ 128/677, 679–683; 364/417

[56] References Cited

U.S. PATENT DOCUMENTS 4,461,266 7/1984 Hood, Jr. et al. .................. 128/681
4,564,020 1/1986 Link ..................................... 128/677

FOREIGN PATENT DOCUMENTS 2846530 7/1979 Fed. Rep. of Germany.

Primary Examiner—Lee S. Cohen
Attorney, Agent, or Firm—Wegner & Bretschneider

[57] ABSTRACT

An electronic blood pressure meter including a cuff, a pressure system for pressurizing and evacuating the cuff, a pressure sensor for detecting pressure within the cuff and a pulse wave sensor for detecting the pulse wave component during the course of cuff pressure changes. The pulse wave sensor produces signals from which a pulse wave amplitude means extracts pulse wave amplitude in time sequence. The maximum value of the pulse wave amplitude is determined and maximum values of the pressure graph area on the higher and lower cuff pressure sides are determined. From these data blood pressure values are calculated 3 Claims, 31 Drawing Figures

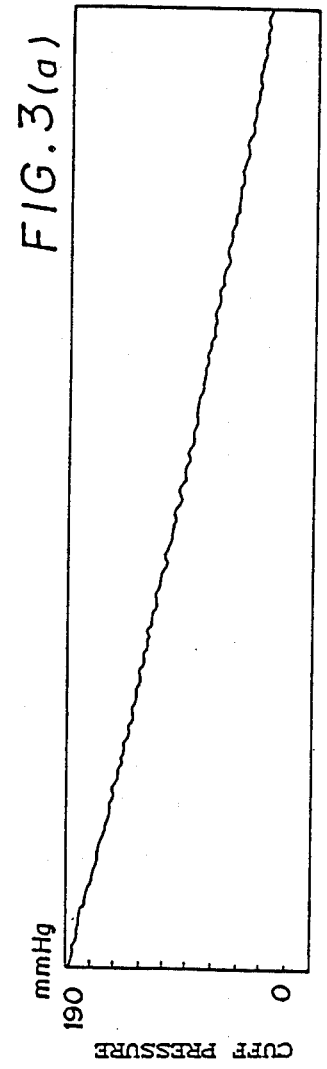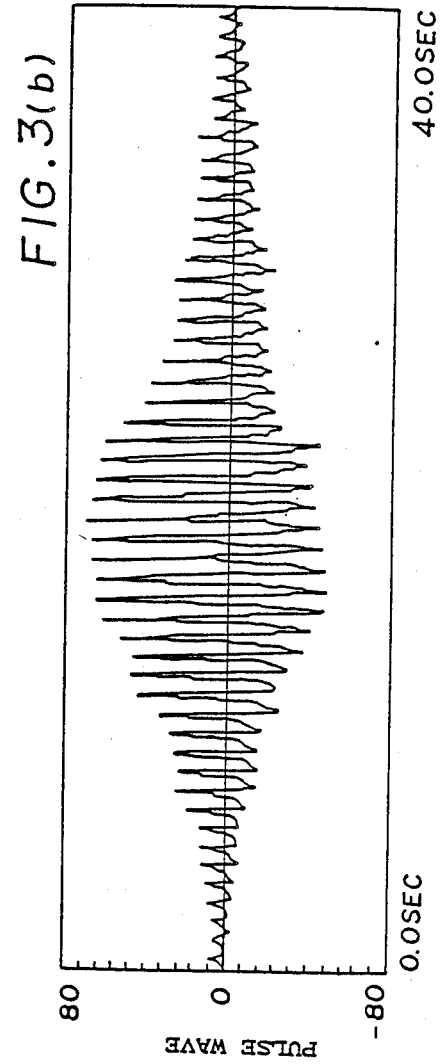

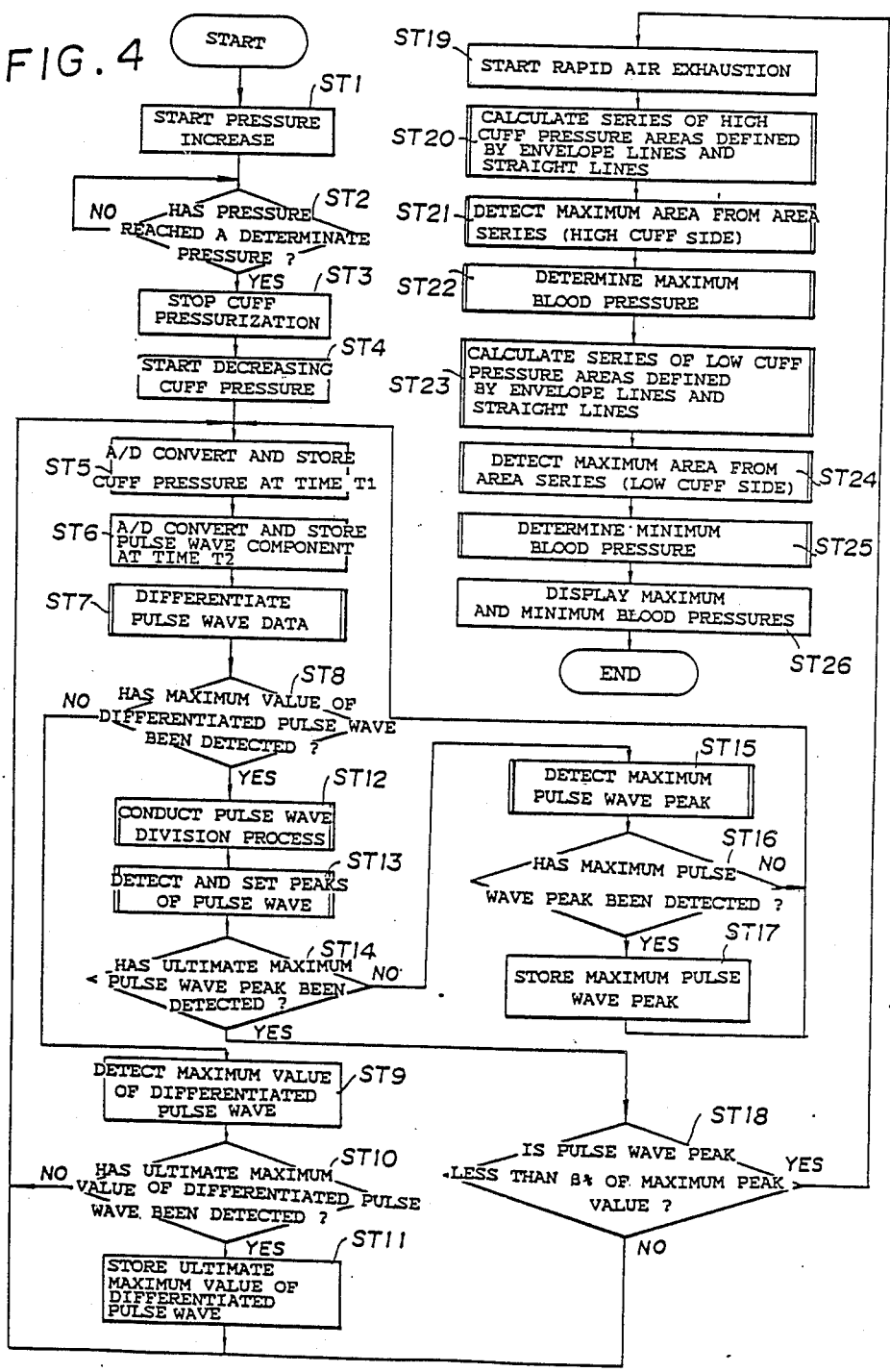

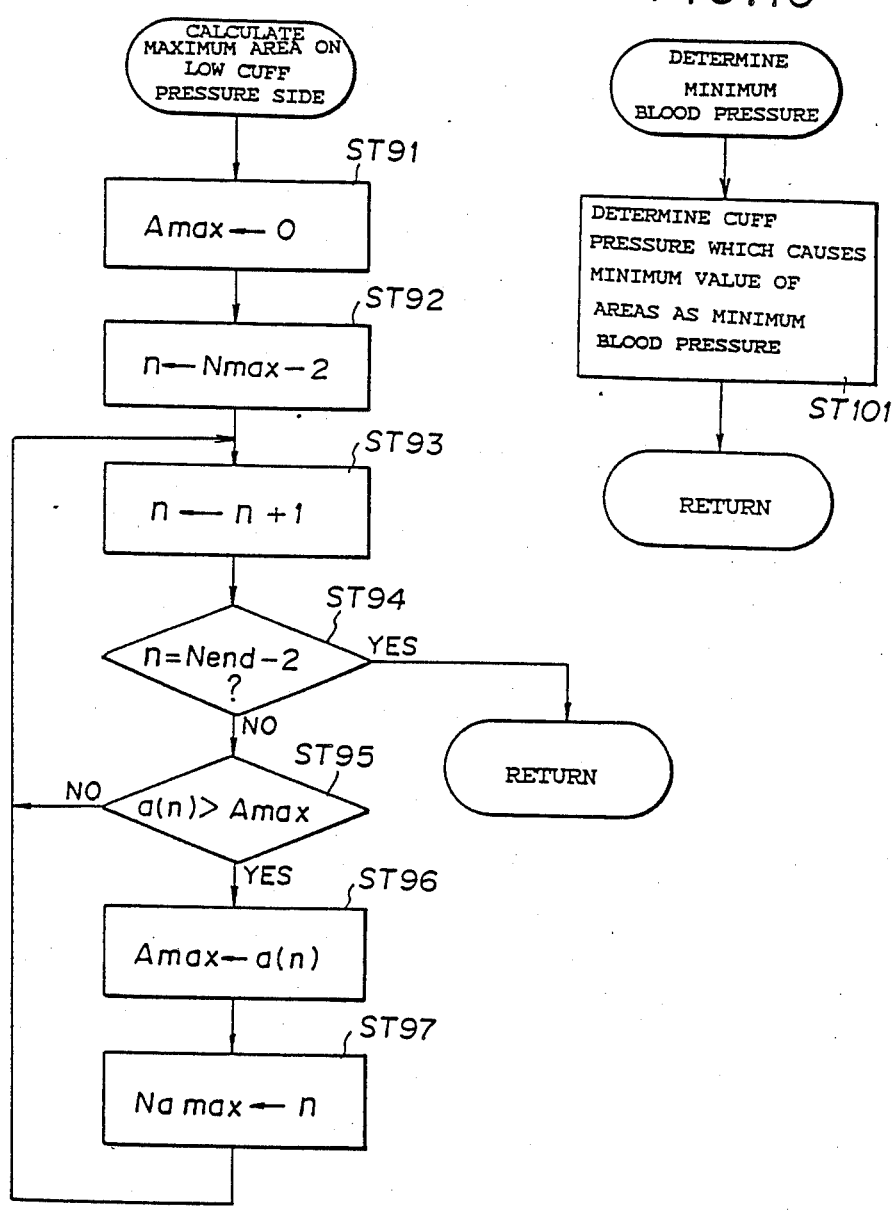
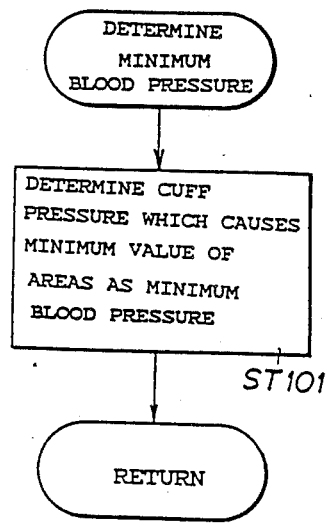

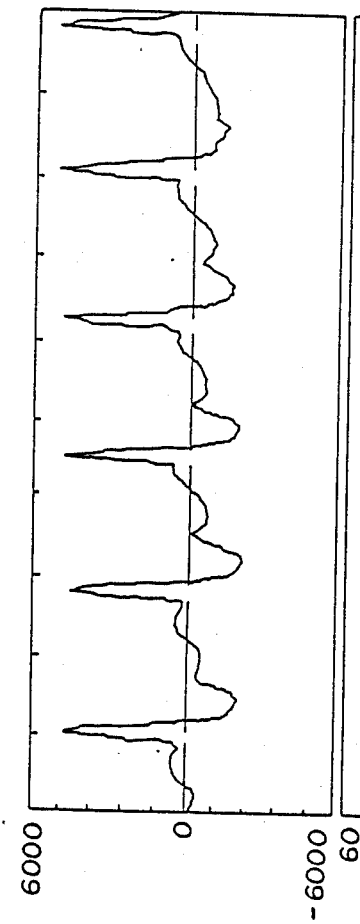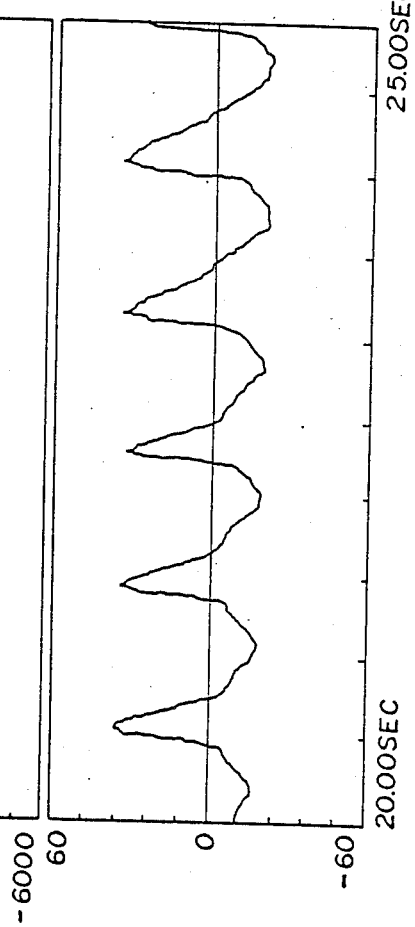
FIG.11(a)
FIG.11(b)

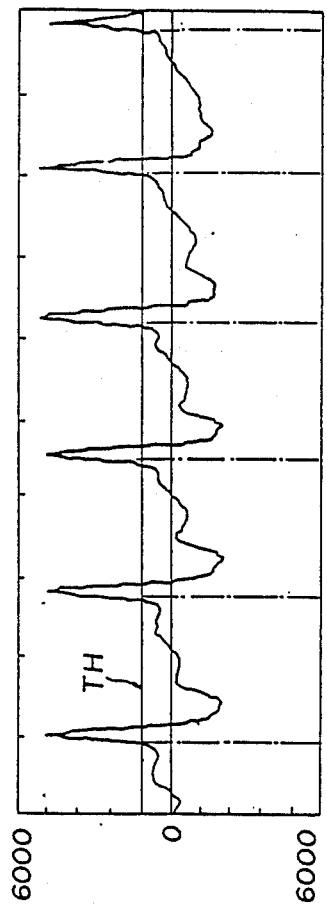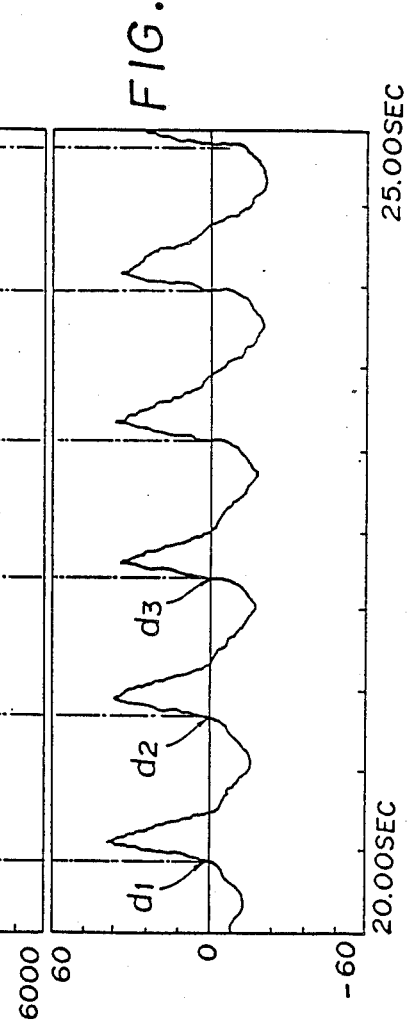

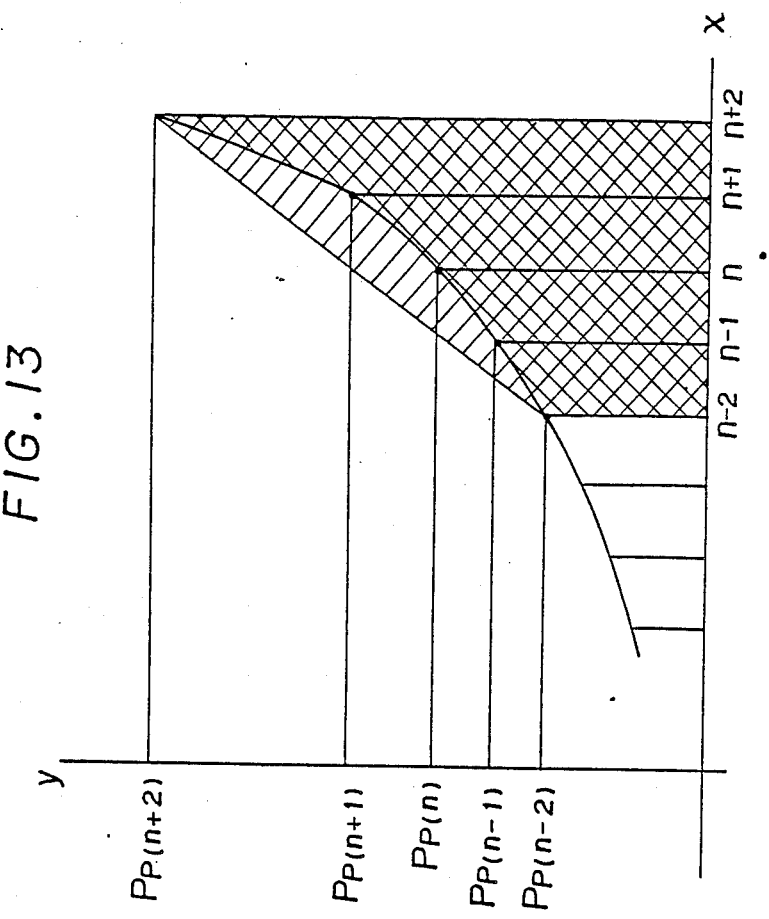

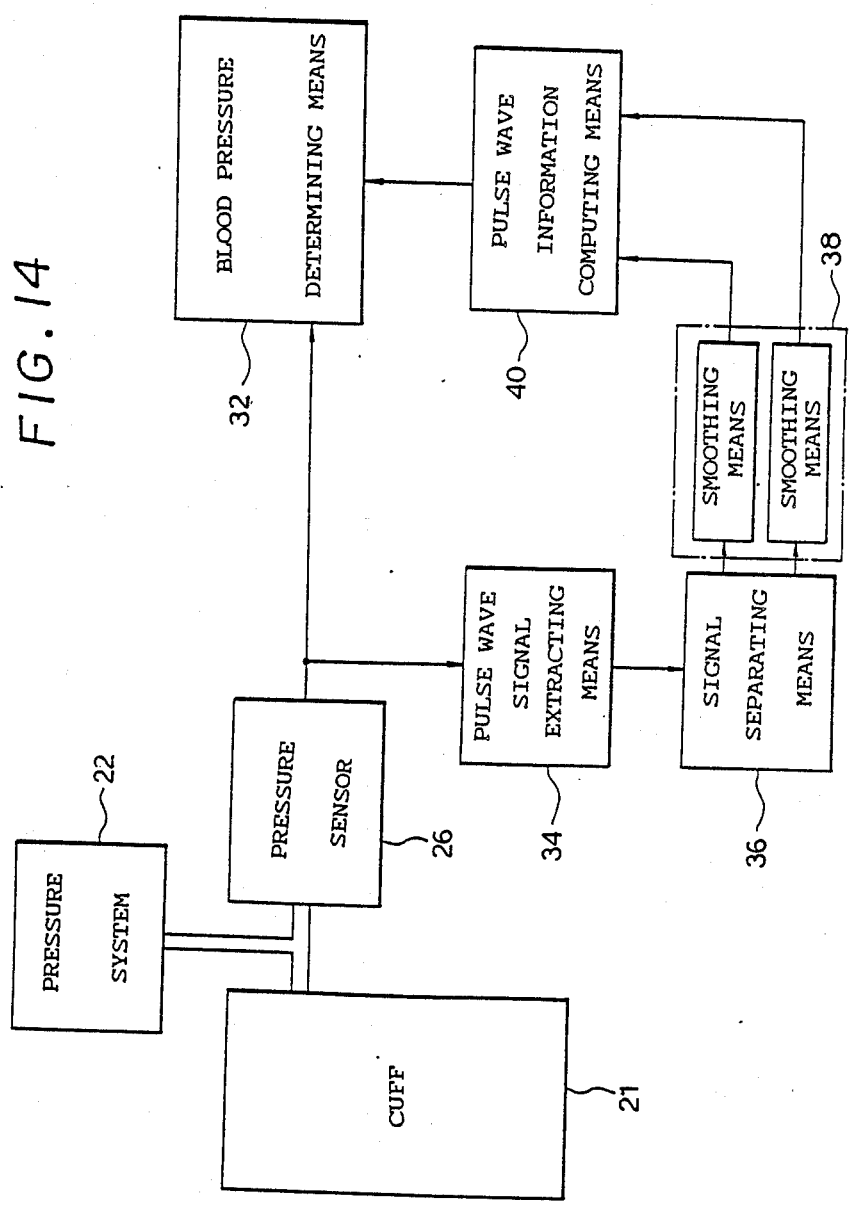

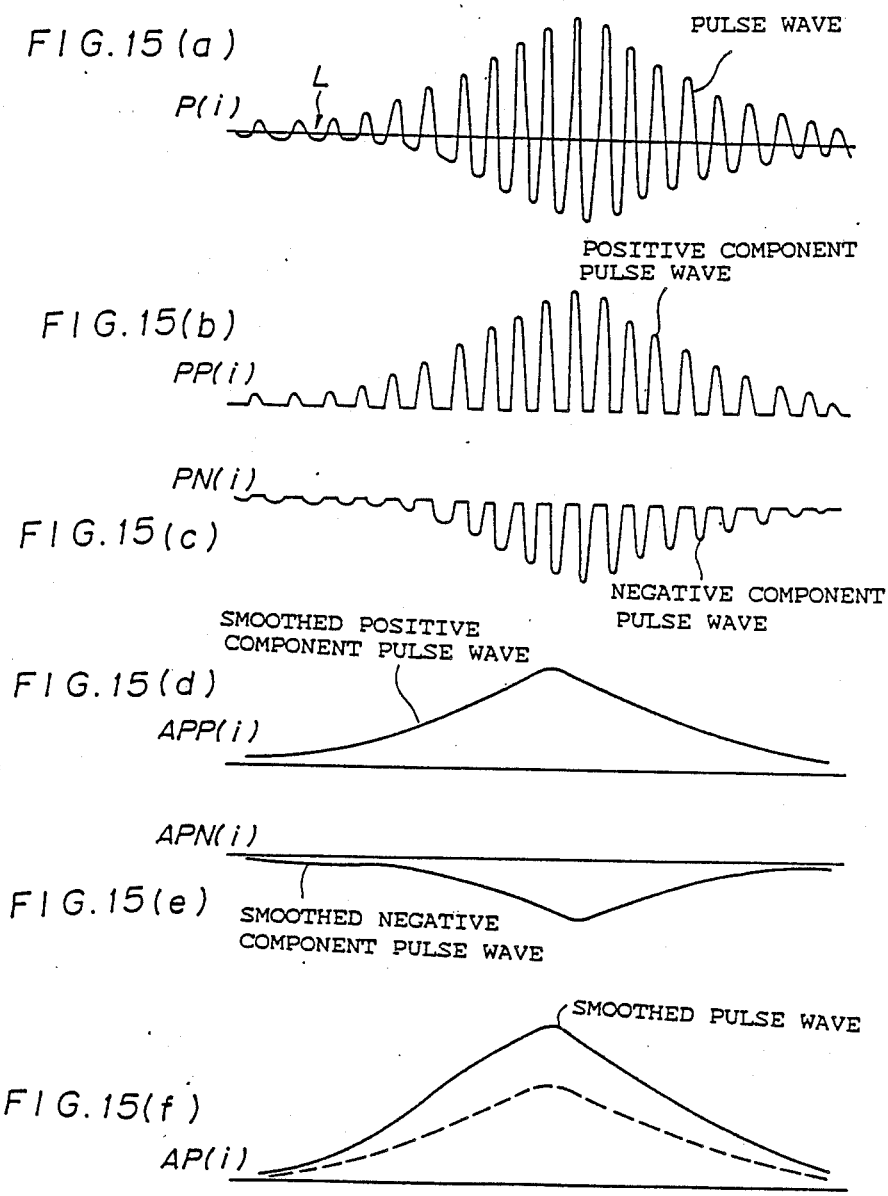

ELECTRONIC BLOOD PRESSURE MEASURING DEVICE

BACKGROUND OF THE INVENTION

The present invention relates to the field of electronic blood pressure measuring devices, and in particular relates to an electronic blood pressure measuring device which measures blood pressure by detecting the amplitude of a pulse wave and to an electronic blood pressure measuring device which determines blood pressure according to smoothed pulse wave information.

According to a prior art type of electronic blood pressure measuring device based upon the so called oscillation method, a cuff is wound on the upper arm of the person whose blood pressure is desired to be measured, such as a patient, and, after the cuff is pressurized to a certain pressure level, wave form information is detected from the cuff pressure and a pulse wave component contained in the cuff pressure during the depressurization of the cuff is isolated, so that the average blood pressure, the maximum blood pressure, and the minimum blood pressure of the person whose blood pressure is being measured may be determined from such data, by finding the amplitude of the pulse wave for each heart beat, and determining the blood pressure from the variation curve (envelope line) of the pulse wave amplitude values and the cuff pressure.

In such an electronic blood pressure measuring device, conventionally the cuff pressure associated with each interval is determined as the cuff pressure at the beginning or at the end of the corresponding time interval. However, according to such a conventional electronic blood pressure measuring device, since the cuff pressure corresponding to each time interval is read out from the cuff pressure at the beginning or at the end of the corresponding time interval, the time points at which the pulse wave appears as its maximum value and minimum value in each interval are different from the time point at which the cuff pressure is read, and therefore some error has in the prior art existed between the parameter (maximum level difference) and the cuff pressure, thereby reducing the accuracy of blood pressure determination provided by the device.

Further, since the pressure value corresponding to the parameter is either at the beginning or at the end of the time interval of the cuff pressure signal in which the pulse wave component is combined and therefore the beginning (or the end) of the interval may correspond either to the maximum point of the pulse wave or to the minimum point of the pulse wave depending upon the particular instance, the curve of the cuff pressure signal tends to oscillate within the amplitude of the pulse wave component, whereby some fluctuations exist in the cuff pressure value, and some distortion exists in the curve of the parameter, thereby reducing the accuracy.

Considering another aspect of the present invention, there is a conventionally known blood pressure measuring technology, known as the Riva-Rocci-Korotkoff method or the auditory method, which has been for some time known as a blood investigation method. According to an electronic blood pressure measuring device based upon this Riva-Rocci-Korotkoff method, after a cuff is wound around the arm of a patient and the cuff is pressurized for stopping blood flow, as the pressure is reduced gradually, the blood starts flowing and a certain distinctive blood sound (the so called Korotkoff sound) is produced, which is detected by a microphone or the like, and then subsequently this sound diminishes as further depressurization of the cuff progressively takes place. The cuff pressure at which the Korotkoff sound is started is then determined as being the maximum blood pressure of the patient, and the cuff pressure at which the Korotkoff sound disappears is determined as being the minimum blood pressure of the patient, in determining the blood pressure of the patient.

As another blood pressure measuring technology, inserting a cannulae into the artery of a patient is known as a blood investigative method.

However, according to an electronic blood pressure measuring device based upon the Riva-Rocci-Korotkoff method among such auditory type conventional blood pressure measuring technologies, the obtained Korotkoff sound is a very small amplitude type signal and its frequency range is from 30 Hz to 150 Hz. Thus, there has been a problem that, since this frequency range tends to be affected by external noises and oscillation noises, especially external and oscillation noises containing the same frequency range or similar frequency ranges, these noises could become a cause of erroneous detection, and such effects have often caused errors in blood pressure measurements in prior art devices for blood pressure measurement by the auditory method. Also, it is hard to recognize any Korotkoff sound from an infant or an adult who is in a state of shock, and in such cases measurement of blood pressure by the auditory method is sometimes impossible. Further, according to such an electronic blood pressure meter based upon the auditory method, since a sensor (such as a microphone) for detecting the Korotkoff sound and also a drive circuit therefor are necessary, therefore the cost of the blood pressure meter tends to be high.

And on the other hand, according to a blood pressure measurement based upon a direct method such as introducing a cannulae into a blood vessel of the patient, the pressure of an artery is transmitted to an external blood pressure transducer by way of a cannulae filled with physiological saline, and in such a method the length of the cannulae, mixing of bubbles therein, and zero point drifts of the blood pressure transducers could cause errors in blood pressure measurement. These errors can be reduced by proper handling, but such handling requires skill and care, thus requiring certain hard to provide techniques in carrying out proper blood pressure measurements. Furthermore, such direct methods as described above have the serious disadvantages that such invasive procedures inevitably cause pain, discomfort, and mental strain to the patient, and increase the possibility of blood tube pain and infections.

Further, according to a conventional type of electronic blood pressure meter based upon the oscillation method, the amplitude of the pulse wave corresponding to the changes in the cuff pressure must be detected, and in order to detect the pulse wave amplitude for each heart beat it is necessary to separate the pulsation on the pulse wave signal which is continuous for each pulse beat. This recognition and separation of pulsations are conducted by feeding the pulse wave signal into a CPU of a microcomputer or the like as pulse wave data and executing a program in the CPU. Therefore, because complicated arithmetic processing is required, a microcomputer having a memory (ROM) of relatively large capacity is necessary, and furthermore the development of the program therefor is difficult, thereby increasing the cost of the electronic blood pressure meter. Also, if the patient has an irregular pulse, or if his or her pulse is relatively weak, the recognition of the pulse beat may not be properly performed, and sometimes accurate measurement of blood pressure becomes impossible. Further, if the patient moves his or her arm during measurement, accurate measurement of blood pressure becomes impossible, because the recognition of the pulse beat is not performed properly, or because the pulse wave amplitude cannot be detected accurately.

SUMMARY OF THE INVENTION

Accordingly, it is the primary object of the present invention to provide an electronic blood pressure measuring device, which avoids the above described problems.

It is a further object of the present invention to provide an electronic blood pressure measuring device in which the pulse wave oscillations do not affect the reading of the cuff pressure.

It is a further object of the present invention to provide an electronic blood pressure measuring device which does not engender pain or discomfort to the patient.

It is a further object of the present invention to provide such an electronic blood pressure measuring device, which does not suffer unduly from external noise.

It is a further object of the present invention to provide such an electronic blood pressure measuring device, which does not suffer from oscillation noise.

It is a further object of the present invention to provide such an electronic blood pressure measuring device, which can measure blood pressure with greater accuracy.

It is a further object of the present invention to provide such an electronic blood pressure measuring device, which is relatively simple in construction.

It is a yet further object of the present invention to provide such an electronic blood pressure measuring device, which is of comparatively low cost.

It is a yet further object of the present invention to provide such an electronic blood pressure measuring device, which allows the processing burden on a CPU incorporated therein to be reduced.

It is a further object of the present invention to provide such an electronic blood pressure measuring device, which allows said CPU incorporated therein to be a CPU of relatively small memory capacity.

It is a yet further object of the present invention to provide such an electronic blood pressure measuring device, which allows the programs for said CPU incorporated therein to be relatively simple to develop.

It is a yet further object of the present invention to provide such an electronic blood pressure measuring device, which does not require the pulse wave to be recognized for each pulse beat.

It is a yet further object of the present invention to provide such an electronic blood pressure measuring device, which is suitable for measuring the pulse of a person who has a relatively irregular pulse.

It is a yet further object of the present invention to provide such an electronic blood pressure measuring device, which is suitable for measuring the pulse of a person who has a relatively weak pulse.

It is a yet further object of the present invention to provide such an electronic blood pressure measuring device, which is suitable for measuring the pulse of a person who is in a state of shock.

It is a yet further object of the present invention to provide such an electronic blood pressure measuring device, which is suitable for measuring the pulse of an infant.

It is a yet further object of the present invention to provide such an electronic blood pressure measuring device, the accuracy of the measurement provided by which is not substantially deteriorated even if the patient moves his or her arm during the measurement process.

It is a yet further object of the present invention to eliminate the types of conventional electronic blood pressure meters based upon the auditory method and/or the oscillation method.

According to one aspect of the present invention, these and other objects are accomplished by an electronic blood pressure meter, comprising: (a) a cuff; (b) a pressure system for pressurizing and evacuating said cuff; (c) a pressure sensor for detecting the pressure within said cuff; (d) a pulse wave sensor for detecting the pulse wave component in the course of cuff pressure changes; (e) a pulse wave amplitude extraction means for extracting the pulse wave amplitude in time sequence; (f) a pulse wave maximum amplitude extraction means for extracting the maximum value of the pulse wave amplitude; (g) an area computing means for computing the area between an envelope line of a certain number of data, including representative data which is extracted in said time sequence, and a line connecting the terminal end data of said data in a sequential manner while shifting the representative data; (h) a first maximum area value extracting means for finding the maximum value of the area computed on the higher cuff pressure side than the cuff pressure corresponding to the maximum value of the amplitude of the pulse wave; (i) a second maximum area value extracting means for finding the maximum value of the area computed on the lower cuff pressure side than the cuff pressure corresponding to the maximum value of the amplitude of the pulse wave; and: (j) a blood pressure determining means for determining a maximum blood pressure from the cuff pressure corresponding to the maximum area extracted by said first maximum area value extracting means, and a minimum blood pressure from the cuff pressure corresponding to the maximum area extracted by said second maximum area value extracting means; and, according to another aspect of the present invention, these and other objects are accomplished by an electronic blood pressure meter, comprising: (a) a cuff; (b) a pressure system for pressurizing and evacuating said cuff; (c) a pressure sensor for detecting the pressure within said cuff; (d) a pulse wave extraction means for extracting the pulse wave component overlaid in said cuff internal pressure; (e) a signal separating means for separating the pulse wave signal into a signal component which is greater than a reference value and another signal component which is smaller than said reference value; (f) a smoothing means for separately smoothing said separated two signal components; (g) a pulse wave information computing means for computing pulse wave information by combining said two smoothed signal components; and: (h) a blood pressure determining means for determining blood pressure according to said pulse wave information and said cuff pressure value obtained from said pressure sensor.

According to the present invention as firstly defined above, during the depressurization process after the pressurization of the cuff by the pressure system, the cuff pressure, a pulse wave component, and the pulse wave amplitude are detected. And for each certain number of data of the pulse wave amplitude, the area surrounded by an envelope line of the data and straight lines connecting data are computed in time sequence. And the maximum areas are extracted from the high pressure side and the low pressure side with respect to the cuff pressure corresponding to the maximum amplitude of the pulse wave, and cuff pressures corresponding to the maximum areas extracted on the high pressure side and the low pressure side are determined, so that the maximum blood pressure and the minimum blood pressure can be determined from these cuff pressures. Since the pulse wave component used for determining the blood pressures is extremely low in frequency having a frequency range of 1 Hz to 19 Hz, it is not susceptible to external noises and/or oscillation noises.

On the other hand, according to the present invention as secondly defined above, as schematically illustrated in FIG. 14 of the accompanying drawings, during the depressurization process after the cuff 1 has been pressurized by the pressure system 2, the cuff pressure is detected by the pressure sensor 3, while the pulse wave signal as exemplarily shown in FIG. 15a is extracted by the pulse wave signal extracting means 4. And with respect to a reference value L, this pulse wave signal is separated into a positive component pulse wave shown in FIG. 15b and a negative component pulse wave shown in FIG. 15c by the signal separating means 5, and after these pulse wave components are smoothed by the smoothing means 6 to produce a smoothed positive component pulse wave as shown in FIG. 15d and a smoothed negative component pulse wave as shown in FIG. 15e, these smoothed positive and negative pulse wave components are combined by the pulse wave information computing means 7 to produce the smoothed pulse wave information as exemplarily shown in FIG. 15f so that the blood pressure may be determined by the blood pressure determination means 8 from this pulse wave information and the cuff pressure. Thus, according to this aspect of the present invention, the algorithm for determining the blood pressure is arbitrary. For instance, the cuff pressure corresponding to the maximum value of the pulse wave information may be determined as the average blood pressure, the cuff pressure on the higher cuff pressure side corresponding to 50% of the maximum value of the pulse wave information as may be determined as the maximum blood pressure, and the cuff pressure on the lower cuff pressure side corresponding to 70% of the maximum value of the pulse wave information may be determined as the minimum blood pressure.

BRIEF DESCRIPTION OF THE DRAWINGS

The present invention will now be shown and described with regard to certain of the preferred embodiments thereof, and with reference to the illustrative drawings, which however should not be considered as limitative of the present invention in any way, since the scope of the present invention is to be considered as being delimited solely by the accompanying claims, rather than by any particular features of the disclosed embodiments or of the drawings. In these drawings:

FIG. 1 is a drawing for illustrating the outline of the operation of the first preferred embodiment of the electronic blood pressure measuring device according to this invention.

FIGS. 3a and 3b are drawings showing the changes in the cuff pressure and the pulse wave amplitude during the depressurization of the cuff pressure in this first preferred embodiment electronic blood pressure measuring device;

FIG. 4 is a flow diagram showing the overall operation of a main program for a microprocessor incorporated in said first preferred embodiment electronic blood pressure measuring device;

FIG. 9 is a flow diagram showing in greater detail the control flow of a routine, which is again invoked from said main program, for the computation of the maximum areas on the lower cuff pressure side;

FIG. 10 is a flow diagram showing in greater detail the control flow of a routine, which is yet again invoked from said main program, for the determination of the minimum blood pressure;

FIGS. 11a and 11b are wave form diagrams for illustrating the differentiated pulse wave wave form and pulse wave wave form of said first preferred embodiment of the electronic blood pressure measuring device of the present invention;

FIGS. 12a and 12b are wave form diagrams for showing the differentiated pulse wave wave form and the pulse wave wave form for illustrating the division of the pulse wave in said first preferred embodiment electronic blood pressure measuring device;

FIG. 13 is a drawing for showing the derivation of the partial areas in the higher cuff pressure side in said first preferred embodiment electronic blood pressure measuring device;

FIG. 14 is a block diagram schematically showing the structure of the second preferred embodiment of the electronic blood pressure measuring device of the present invention;

FIG. 15 shows a plurality of pulse wave forms for illustrating said second preferred embodiment of the present invention: FIG. 15a shows an exemplary wave form for the pulse wave component, FIG. 15b shows the wave form of the positive pulse wave component, FIG. 15c shows the wave form of the negative pulse wave component, FIG. 15d shows the smoothed wave form of the positive pulse wave, FIG. 15e shows the smoothed wave form of the negative pulse wave, and FIG. 15f shows the smoothed wave form of the pulse wave;

DESCRIPTION OF THE PREFERRED EMBODIMENTS

The present invention will now be described with reference to the preferred embodiments thereof.

Figure 2:
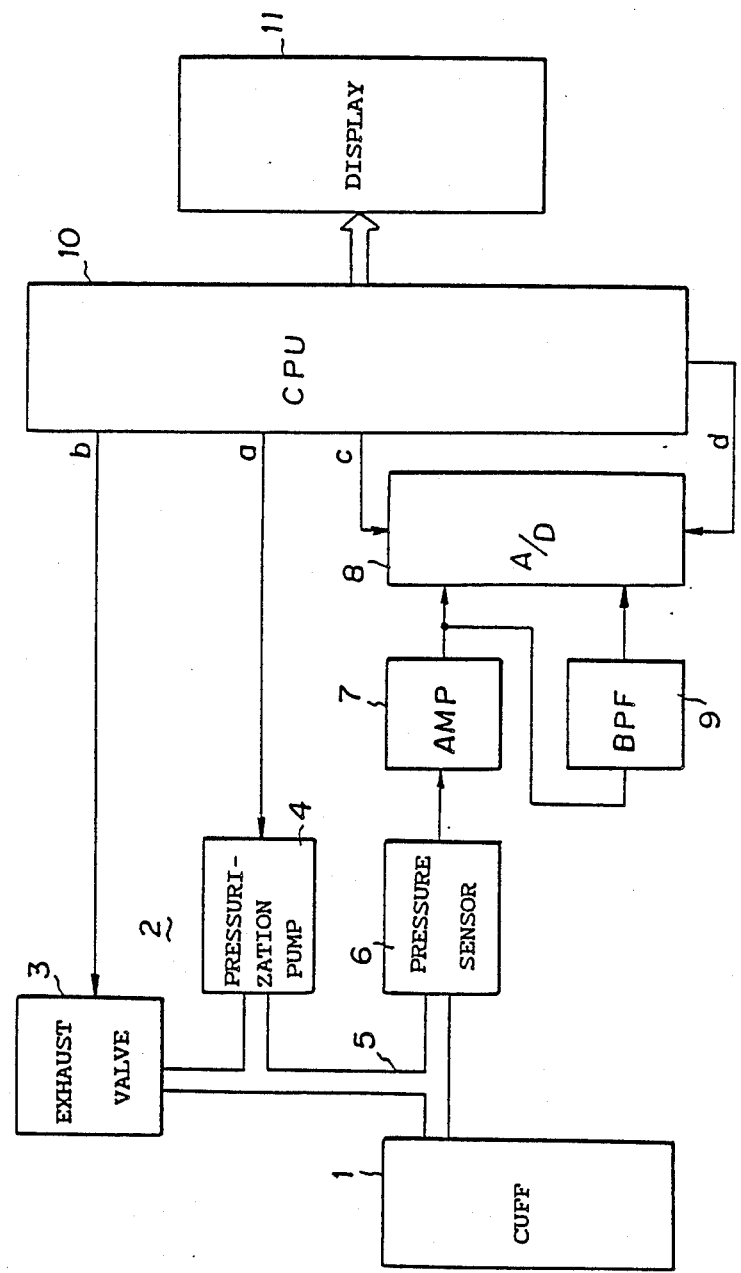
FIG. 2 is a block diagram of the first preferred embodiment of the electronic blood pressure measuring device of the present invention.

FIG. 2 is a block diagram of an electronic blood pressure measuring device which is a first preferred embodiment of the electronic blood pressure measuring device of the present invention. In FIG. 2, a cuff 1 is formed as a bag to be wound on the arm of a patient, being as before made of rubber or of some other suitable flexible material, and this cuff 1 is connected to a pressure system 2 comprising an exhaust valve 3 and a pressurization pump 4 by way of a branched rubber tube 5. A pressure sensor 6 is connected to the cuff 1 by way of the rubber tube 5 and converts the cuff pressure sensed thereby into an electric signal. The output of the pressure sensor 6 is connected to an input end of an amplifier 7, and the output electric signal of the pressure sensor 6 or the cuff pressure signal is DC amplified by the amplifier 7. The output end of the amplifier 7 is connected to an input end of an A/D converter 8 on the one hand, and to an input end of a band pass filter 9 on the other hand. The output end of the A/D converter 8 is connected to a CPU 10, and so is the output of the band pass filter 9; and thereby the output of the amplifier 7 and the output of the band pass filter 9 are both supplied to the CPU 10 after being converted into digital signals by the A/D converter 8.

The CPU 10 executes predetermined processes according to an internal program stored therein, and has the functions of determining the blood pressure values such as the maximum blood pressure, the maximum blood pressure, and so on, and determined blood pressure values are displayed on a display unit 11.

When a measurement start key which is not particularly shown in the drawing is actuated, the CPU 10 starts the action of the pressurization pump 4 to pressurize the cuff 1 by issuing a command "a", and controls the air exhaust from the exhaust valve 3 by issuing a command "b". And the cuff pressure from the amplifier 7 and the pulse wave component from the band pass filter 9 are read in at certain sampling cycles by commands "c" and "d". According to this electronic blood pressure measuring device, after the cuff 11 is wound around the arm of the patient, and the pressurization pump 4 is actuated by operating the measurement start key until the cuff pressure reaches a certain level, the pressurization pump 4 is stopped and the air exhaust is gradually started by the exhaust valve 3. As the cuff pressure gradually drops, the output signal of the pressure sensor 6 becomes as shown in FIG. 3a and the extracted pulse wave component from the output of the band pass filter 9 or the output from the amplifier 7 becomes as shown in FIG. 3b.

The CPU 10 determines the average blood pressure, the maximum blood pressure, and the minimum blood pressure from the detected cuff pressure and the amplitude value of the pulse wave (peak value) according to a flow which will be described hereinafter. Now, this action will be described with reference to the flow chart of FIG. 4.

First of all, when the measurement start key is pressed and the action is started, the pressurization pump 4 starts its action by the command "a" (in the step ST1), and the cuff 1 is pressurized until a determinate pressure sufficient for measurement is built up (in the step ST2). And, when the cuff pressure reaches a certain predetermined cuff pressure, the action of the pressurization pump 4 is stopped and at the same time as stopping the pressurization (in the step ST3) the exhaust valve 3 begins gradual air exhaustion by the command "b" to begin depressurization (in the step ST4). And by the command "c", for every T1 (for instance 100 ms as an example) the output of the amplifier 7 or the cuff pressure is A/D converted and is stored (in the step ST5). Likewise, by a command, for each T2 (for instance 10 ms in the same example) the output of the band pass filter 9 or the pulse wave component is A/D converted by the A/D converter 8 and is taken in by the CPU and is stored (in the step ST6).

The discrete data of the pulse wave which has been A/D converted is differentiated for each point (in the step ST7). This differentiation is conducted according to the following equation:

$$f(n) = \frac{\sum_{j=1}^{m} \{f(n+j) - f(n-j)\} \times j}{k}$$

where n=1, 2, 3 and so on, k is a normalization constant (k=110 in the illustrative example), and f(n) is an original data with n selected as 5 in the example.

FIG. 11 shows the wave forms of the pulse wave before and after the differentiation. FIG. 11a is a differentiated wave form, and FIG. 11b is the pulse wave wave form.

Then the maximum value of the differentiated pulse wave is extracted. Specifically, following the differentiation process in the step ST7, it is determined whether the maximum value of the differentiated pulse wave has been detected or not (in the step ST8), and this detection of the maximum value of the differentiated pulse wave is repeated until such a value is detected (in the step ST9). This process consists of comparing the current differentiated value and the maximum value up to the point and renewing or updating the maximum value if the current value is greater than the previous maximum value, and if the value is not updated for more than a certain time interval (for instance three seconds) the value is considered as the maximum value of the differentiated pulse wave.

Therefore, when the certain time interval has elapsed without the differentiated value being updated, the determination result for the detection of the maximum value of the differentiated pulse wave in the step ST10 is NO, and the process flow returns to the step ST5 and the process of detecting the maximum value of the differentiated pulse wave is repeated on a real time basis. When the maximum value of the differentiated pulse wave is detected, the determination result of the step ST10 becomes YES, and the maximum value of the differentiated pulse wave is stored (in the step ST11). And the process flow returns to the step ST5, but since the determination result for the detection of the maximum value of the differentiated pulse wave in the step ST8 now becomes YES, the process flow moves on to the step ST12 and conducts a pulse wave division process.

This pulse wave division process consists of setting α percent (α is equal to 10 to 20) of the maximum value of the differentiated pulse wave extracted in the step ST9 as a threshold level, finding an intersecting point between this level and the rising curve of the differentiated pulse wave, and setting the point on the pulse wave wave form corresponding to this intersecting point as a division point. The line TH shown in FIG. 12 is the threshold level, and d1, d2, d3 and so on are division points.

And the maximum value of the pulse wave is detected for each of the intervals defined by this division of the pulse wave (in the step ST13), and these maximum values of the pulse wave are set as the pulse wave peaks. And the maximum value of these pulse wave peaks are obtained for various division intervals. The detection of the maximum peak value of the pulse wave consists of comparing the current pulse wave peak value to the preceding pulse wave peak values, and if the current pulse wave peak value is greater than the previous ones the greater pulse wave is stored as updating data, and if no updating takes place for more than a certain time interval the pulse wave peak value is stored as the maximum peak value of the pulse wave (in the step ST17). The cuff pressure corresponding to this maximum peak value of the pulse wave is stored as an average blood pressure CM.

When the maximum peak value of the pulse wave is stored, the determination result on the detection of the maximum peak value of the pulse wave in the step ST14 becomes YES, and then it is determined whether or not the pulse wave peak value is equal to or less than β percent (β is equal to 40 to 60%) of the maximum peak value (in the step ST18). If it is not equal to or less than β%, the process flow returns to the step ST5 and the processes including the cuff pressure A/D conversion, storage (in the step ST5), pulse wave A/D conversion, storage (in the step ST6), the pulse wave peak detection (in the step ST14) and so on are repeated.

When the pulse wave peak becomes equal to or less than β% of the maximum peak, the determination result of the step ST18 becomes YES, meaning that the pulse wave peak value which is necessary for measurement has already been measured in this state, and a command "b" is outputted from the CPU 10 to the exhaust valve 3. As a result, the exhaust valve 3 starts rapid air exhaustion (in the step ST19).

Thus, the real time processes such as differentiation of the pulse wave, detection of pulse wave peaks, and so on in the depressurization process of the cuff pressure are completed. Thereafter, certain processes are executed on the pulse wave peak values obtained in this real time process, and subsequent thereto the process of determining the maximum blood pressure and the minimum blood pressure is to be started. Now, the process of determining blood pressures will be described in the following.

After rapid air exhaustion, a row of areas (a(n)) defined by the envelope lines and the straight lines are computed with respect to the group of data of the extracted pulse wave peaks (PP(n)) on the higher cuff pressure side of the pulse wave maximum peak (Pmax) (in the step ST20).

A concrete example of the computations of the areas a(n) will be described in the following with reference to FIG. 13.

In FIG. 13, n on the x axis denotes pulse wave serial numbers, while the y axis represents corresponding pulse wave peaks. The area a(n) represented by the pulse wave number n is obtained by subtracting an area defined by points $(n-2,0)$, $(n+2,Pp(n+2))$, $(n-1,Pp(n-1))$, $(n,Pp(n))$, $(n+1,Pp(n+1))$, $(n+2,Pp(n+2))$, $(n+2,0)$ from a trapezoidal area defined by points $(n-2,0)$, $(n-2,Pp(n-2))$, $(n+2,Pp(n-2))$, and $(n+2,0)$.

The trapezoidal area defined by points $(n-2,0)$, $(n-2,Pp(n-2))$, $(n+2,Pp(n-2))$, and $(n+2,0)$ is found as $\frac{1}{2} \cdot 4h(Pp(n+2)+Pp(n-2))$ if the interval h is between a point (i,0) and a point (i+1, 0) (where i is from $n-2$ to $n+1$).

Meanwhile the trapezoidal area Q(i) defined by the points (i,0), (i,Ppi), (i+1,Pp(i+1)), and (i+1,0) (where i is from $n-2$ to $n+1$) is $Q(i) = \frac{1}{2}h(Pp(i)+Pp(i+1))$. Therefore, the area a(n) can be expressed by:

$$a(n) = \frac{1}{2}4h(Pp(n+2) + Pp(n-2)) - \sum_{i=n-2}^{n+1} Q(i)$$

$$= \frac{1}{2}h[4(Pp(n+2) + Pp(n-2)) - \{Pp(n-2) + Pp(n-1)) + (Pp(n-1) + Pp(n)) + (Pp(n) + Pp(n+1)) + (Pp(n+1)) + Pp(n+2))\}]$$

$$= \frac{1}{2}h\{3(Pp(n+2) + Pp(n-2)) - 2(Pp(n-1) + Pp(n) + Pp(n+1))\}$$

If h=1, then a(n) can be derived -as:

$$a(n) = \frac{3}{2}(P_p(n+2) + P_p(n-2) - (P_p(n-1) + P_p(n) + P_p(n+1))\}$$

However, if any one of the points $(n-1,Pp(n-1))$, $(n,Pp(n))$, and $(n+1,Pp(n+1))$ is above a line connecting the points $(n+2,Pp(n+2))$ and $(n-2,Pp(n-2))$, since it means that the envelope line is within the range of the average blood pressure away from the area corresponding to the maximum blood pressure, a(n) is set as zero.

Figure 1A:
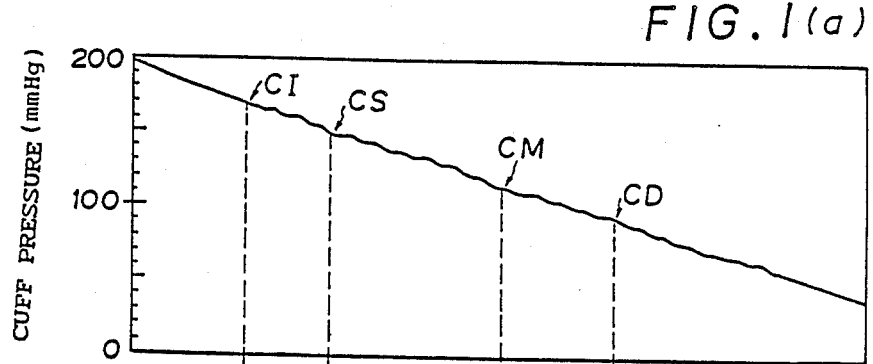
FIG. 1a is a drawing illustrating the process of depressurizing the cuff pressure.
Figure 1B:
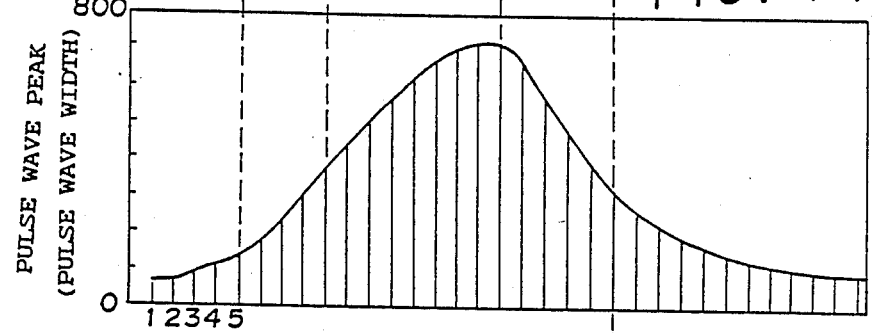
FIG. 1b is a drawing illustrating a series of pulse wave peaks during the depressurization process.
Figure 1C:
FIG. 1c is a drawing illustrating the distribution of the partial areas surrounded by the envelope line and the straight line portion of the pulse wave peaks in time series.

These areas a(n) are computed for each of the pulse wave numbers by incrementing the pulse wave number n for the pulse wave peaks shown in FIG. 1b by 1. And a row or series of areas (a(n)) are computed as shown in FIG. 1c.

Subsequently, a maximum area is detected from the area series (a(n)) (in the step ST21), and setting the cuff pressure value corresponding to the group of the pulse wave series which gives the maximum area value as CI (refer to FIG. 1) the maximum blood pressure value CS is determined from the following equation according to the average blood pressure value CM which has already been extracted and stored (refer to FIG. 1) in the step ST22):

$$CS = \tfrac{2}{3}(CI - CM) + CM$$

The maximum blood pressure determined from this equation has been experimentally confirmed to be proper and practical.

Next, a series of areas a(n) surrounded by the envelope line and the straight lines are computed in the same way as in the step ST20 with respect to a series of data of the extracted pulse wave peaks PP(n) on the lower cuff pressure side of the pulse wave maximum peak (Pmax) (in the step ST23).

Subsequently, the maximum area is derived from the series of areas a(n), (refer to the right hand side of FIG. 1c) (in the step ST24), the maximum blood pressure value is determined from the cuff pressure value CD (refer to FIG. 1a) corresponding to the maximum value of the areas (in the step ST25). And, the maximum blood pressure and the minimum blood pressure are displayed on the display unit 11 (in the step ST26), and the measurement is completed.

Now, the specific processes in the subroutines invoked from the step ST20 to the step ST25 in the main flow will be described in the following.

Explanation of computation of the series of areas on the high cuff pressure side (in the step ST20)

Figure 5:
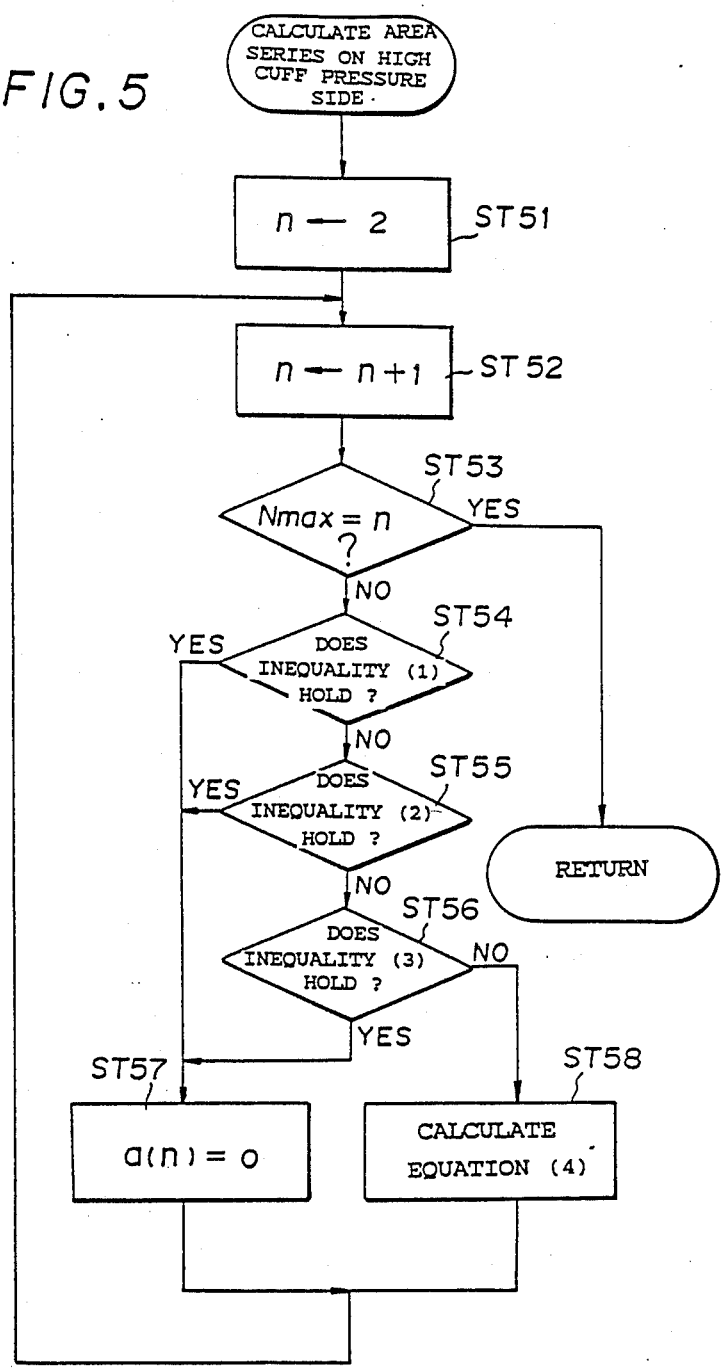
FIG. 5 is a flow diagram showing in greater detail the control flow of a routine, which is invoked from said main program, for the derivation of a series of areas on the higher cuff pressure side.

Upon entering the step ST20 in the main flow, the pulse wave number n is set to 2 (in the step ST51), as shown in the flow chart of FIG. 5, and 1 is added to n (in the step ST52), and it is determined whether or not nmax=n or not (in the step ST53). Here, nmax is an integer which causes Pmax to be equal to PP(nmax) (the cuff pressure corresponding to this nmax is the average blood pressure·CM), and as long as the determination result is NO in the step ST53, the computation of the areas on the high cuff pressure side is to be executed. In other words, if the determination result of the step ST53 is NO, it is determined whether the following inequalities hold or not (in the step ST54, the step ST55, the step ST56):

$$Pp(n) > \frac{Pp(n-2) + Pp(n+2)}{2} \quad (1)$$

$$Pp(n-1) > \frac{\left(\left(\frac{Pp(n-2) + Pp(n+2)}{2}\right) + Pp(n-2)\right)}{2} \quad (2)$$

$$Pp(n+1) > \frac{\left(\left(\frac{Pp(n-2) + Pp(n+2)}{2}\right) + Pp(n+2)\right)}{2} \quad (3)$$

If any one of these inequalities holds, it means that either PP(n), PP(n−1), or PP(n+1) is located above the straight line previously identified, and therefore the area a(n) is determined as zero (in the step ST57). If none of the inequalities holds, then the equation:

$$a(n) = \tfrac{3}{2} (P_p(n+2) + P_p(n-2) - (P_p(n-1) + P_p(n) + P_p(n+1))) \quad (4)$$

is executed (in the step ST58), and after the process flow has returned to the step ST52 n is incremented by one and the computation of the areas is repeated. In the step ST53, if nmax is equal to n, the computation of a(n) on the higher cuff pressure side is complete and the system flow returns to the main flow.

Explanation of computation of the maximum area on the high cuff pressure side (in the step ST21)

Figure 6:
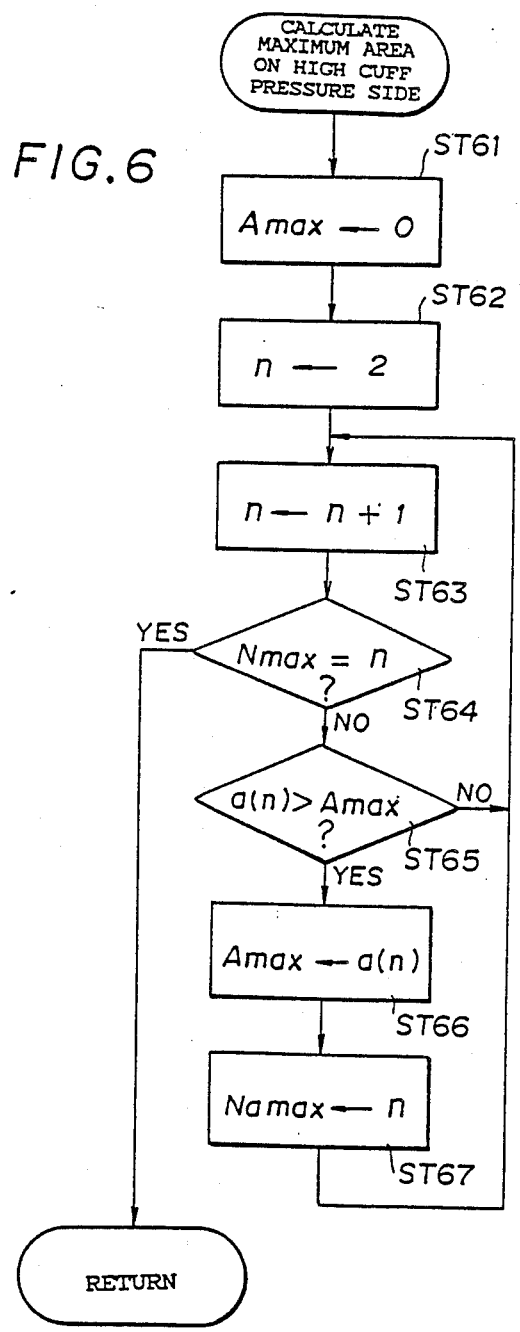
FIG. 6 is a flow diagram showing in greater detail the control flow of a routine, which is again invoked from said main program, for derivation of the maximum area values on the higher cuff pressure side.

Upon entering the step ST21 in the main flow, as shown in the flow chart of FIG. 6, the maximum value of the area Amax is set to zero (in the step ST61). And n is set to 2 (in the step ST62) and after unity is added to n (in the step ST63) it is determined whether or not nmax is equal to n or not (in the step ST64). And until this determination result becomes YES, the maximum value of the area amax is compared with the sequentially read out area values a(n) (in the step ST65), and if the read out area value a(n) is smaller than the maximum value the system flow returns as it is to the step ST63, but if the area value a(n) is greater than the maximum value this area value a(n) is used for updating the maximum area value amax (in the step ST66). And the value of n at this particular point is stored as nmax as being corresponding to the maximum area value amax (in the step ST67) and after the system flow has returned to the step ST63 n is incremented by unity to repeat the update process of the maximum area value amax thereafter. In the step ST64, if nmax is equal to n, the derivation of the maximum area on the high cuff pressure side is complete, and the system flow returns to the main flow.

Explanation of computation of the maximum blood pressure (in the step ST22)

Figure 7:
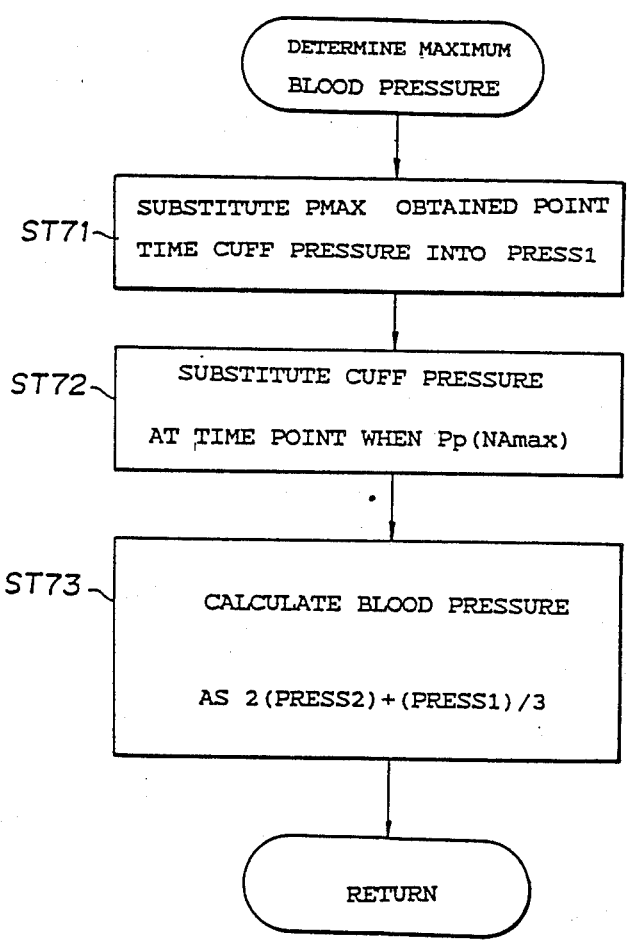
FIG. 7 is a flow diagram showing in greater detail the control flow of a routine, which is again invoked from said main program, for determination of the maximum blood pressure.

Upon entering the step ST22 in the main flow, as shown in the flow chart of FIG. 7, the cuff pressure CM at the time point when the maximum value Pmax of the pulse wave peak was obtained is substituted into PRESS1 (in the step ST71). Subsequently, the cuff pressure CI at the time point when the pulse wave peak Pp(Namax) maximizes the area is substituted into PRESS2 (in the step ST72). And by carrying out the computation (2(PRESS2)+(PRESS1))/3, the maximum blood pressure CS is determined (in the step ST73) before the system flow returns to the main flow.

Explanation of computation of the low cuff pressure side area (in the step ST23)

Figure 8:
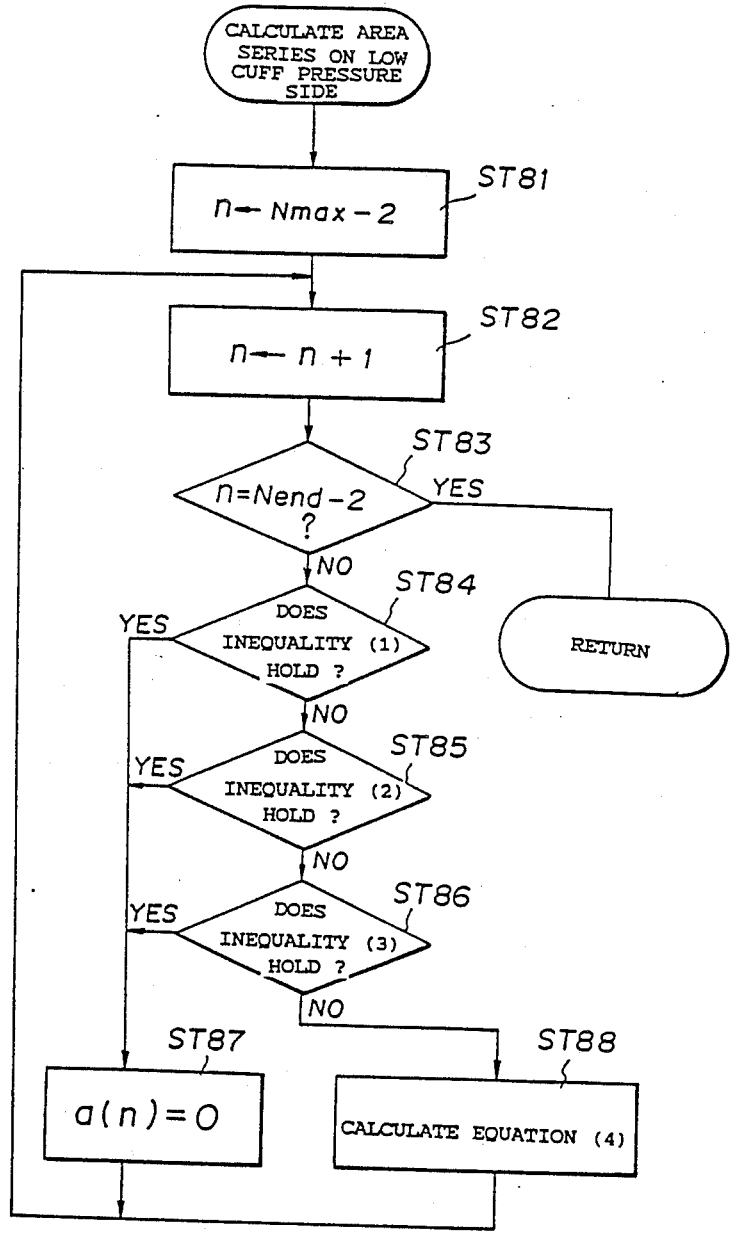
FIG. 8 is a flow diagram showing in greater detail the control flow of a routine, which is again invoked from said main program, for computation of the series of areas on the lower cuff pressure side.

Upon entering the step ST23 in the main flow, as shown in the flow chart of FIG. 8, first n is set to nmax-2 (in the step ST81), and after adding unity to n (in the step ST82) it is determined whether or not n is equal to nend-2 or not (in the step ST83). Here, nend is the serial number of the pulse wave which was extracted last of all. As long as the determination result of the step ST82 is NO, throughout the step ST84 to the step ST86, it is determined whether or not the same inequalities (1), (2), and (3) hold or not, in the same way as in the computation of the series of areas on the higher cuff pressure side described in connection with FIG. 5, and if either one of the inequalities holds a(n) is set to zero (in the step ST87), but on the other hand if none of the inequalities holds then the area a(n) is computed by equation (4) (in the step ST88) before the system flow returns to the step ST82. Thereafter, n is incremented by one in the step ST82, and the computation for the areas is repeated until n becomes equal to nend. In the step ST83, if n equals nend-2, the computation of the areas a(n) on the lower cuff pressure side is completed, and the system flow returns to the main flow.

Explanation of computation of the maximum area on the lower cuff pressure side (in the step ST24)

Upon entering the step ST24 in the main system flow, as shown in the flow chart of FIG. 9, first of all, the maximum value of the areas amax is set to zero (in the step ST91). And n is set to nmax-2 (in the step ST92), and after n is further incremented by one (in the step ST93) it is determined whether or not n is equal to nend-2 or not (in the step ST94). Until this determination result becomes YES, the area values a(n) and the maximum value of the areas amax are compared and the maximum value of the areas amax is updated (in the step ST95, and the step ST96) on the one hand, and the n at which an updating took place is stored as Namax (in the step ST97) before the system flow returns to the step ST93 on the other hand. Thereafter, the update process of the maximum area value amax is repeated. If n is equal to nend-2 in the step ST94, the derivation of the maximum area on the lower cuff pressure side is completed, and the system flow returns to the main flow.

Determination of the minimum blood pressure (in the step ST25)

Upon entering the step ST25 in the main flow, the cuff pressure CD at which the pulse wave peak Pp(Namax) which causes the minimum value of the areas is determined as the minimum blood pressure (in the step ST101 as shown in the flow chart of FIG. 10). After this determination, this system flow returns to the main flow.

Thus, the various blood pressures can be measured from the cuff pressure and the pulse wave. It has been confirmed that the maximum, minimum, and the average blood pressures obtained according to the above described algorithm agree with the blood pressure measurements obtained by the use of Korotkoff sound.

Although in the above described first preferred embodiment a band pass filter was used to extract the pulse wave, according to this invention it is possible to use a digital filter instead, and it is also possible to feed the cuff pressure signal containing a pulse wave signal into a CPU and to separate the cuff pressure signal and the pulse wave component by a software process which is different from a digital filter.

Further, although in the above described first preferred embodiment extraction of the pulse wave peak values was conducted by pulse wave division after deriving the differentiated values of the pulse wave, the extraction of the pulse wave peak values is not to be considered as limited thereby, according to this invention.

Thus, according to the electronic blood pressure measuring device of this first preferred embodiment of the present invention, as opposed to conventional electronic blood pressure measuring devices, since a blood pressure measurement is conducted by making use of information on cuff pressure and the amplitude of the pulse wave which is an oscillation within the cuff pressure, and the frequency range of this pulse wave is as low as from 1 Hz to 10 Hz, by providing a filter of such a band, almost all the external noises and oscillation noises can be eliminated, so that the amplitude information of the pulse wave can be used for processing by arithmetic means without involving any distortion, and accurate blood pressure measurement is possible even in an environment filled with noise. In particular, since the determination of the blood pressure is based upon the computation of the areas surrounded by the envelope line of the pulse wave amplitude which does not contain noise components, and the line connecting both ends of a predetermined number of data to use these partial areas as parameters, the differences in the areas become very conspicuous, and therefore accurate measurement of blood pressure becomes possible.

Now, with reference to FIGS. 14 through 20, a second preferred embodiment of the electronic blood pressure measuring device of the present invention will be described. Reference numerals in FIGS. 14 througn 20 for this second preferred embodiment do not particularly correspond to reference numerals relating to FIGS. 1 through 13 for the first preferred embodiment.

In FIG. 14, shows a cuff to which a pressure system 22 is attached through tubing or the like, so that the cuff may be pumped up and the pressure gradually released. Pressure sensor 26 determines pressure values in the cuff over the period of time that the blood pressure measuring device is in operation. The pressure sensor 26 produces output signals to both the blood pressure determining means 32 and the pulse wave signal extracting means 34. The output of the pulse wave signal extracting means 34 goes to a signal separating means 36, the output of which is passed through smoothing means 38 to pulse wave information computing means 40. Based on the output from the pressure sensor 26 and the pulse wave information computing means 40, blood pressure determining means 32 produces output signals in the form of a display of systolic and diastolic blood pressure readings.

Figure 16:
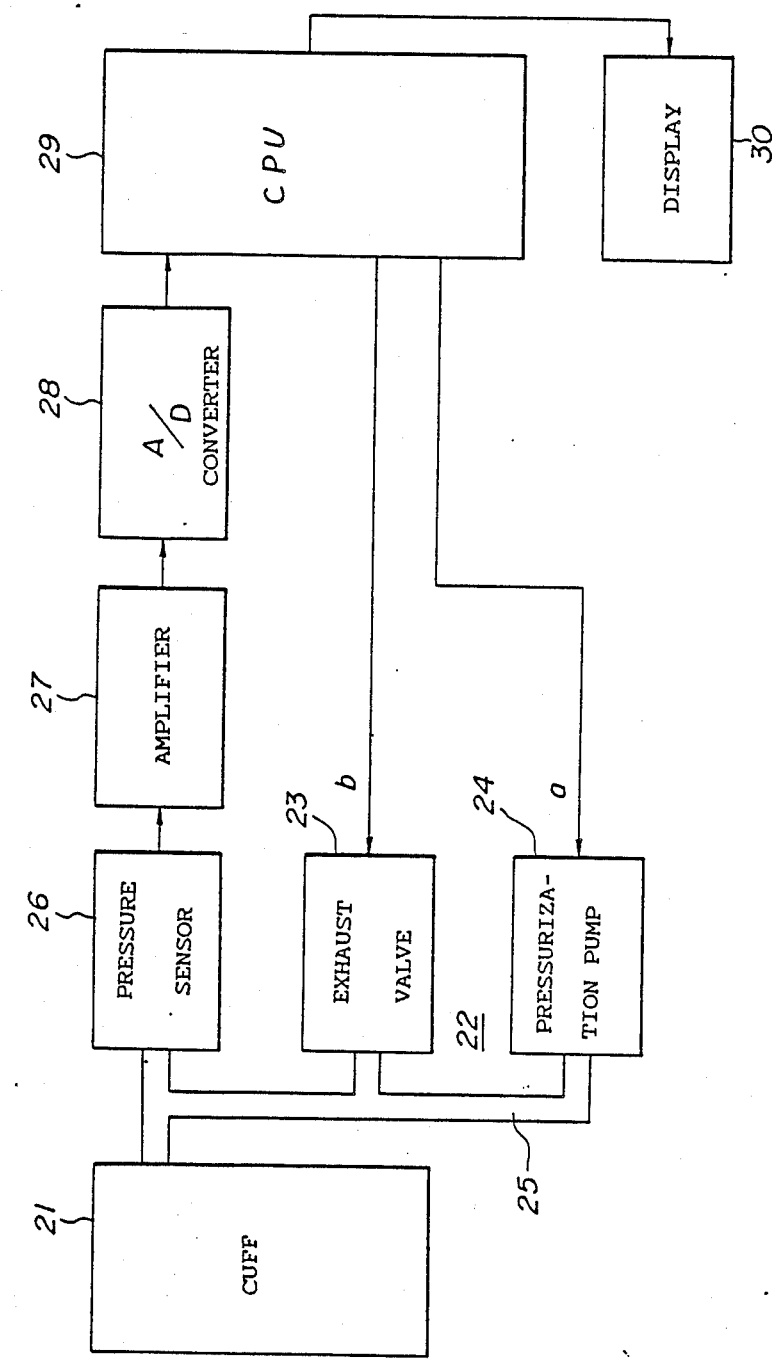
FIG. 16 is a block diagram of said second preferred embodiment of the electronic blood pressure meter according to the present invention.

FIG. 16 is a block diagram of this second preferred embodiment of the electronic blood pressure meter according to the present invention. In this electronic blood pressure meter, separation of the positive and negative components of the pulse wave and smoothing thereof are conducted by program processing in the CPU 29. In this drawing, the reference numeral 21 denotes the cuff which as before is formed as a rubber bag to be wound around the arm to the patient, and this cuff 21 is connected to a pressure system 22 comprising an exhaust valve 23 and a pressurization pump 24 by way of a rubber tube system 25. A pressure sensor 26 is also connected to the cuff 21 by way of the rubber tube system 25, and this pressure sensor 26 converts the cuff pressure into an electric signal.

The output signal of the pressure sensor 26 is amplified by an amplifier 27 and after being converted into a digital signal by an A/D converter 28 is fed into the CPU 29.

The CPU 29 is internally equipped with memory such as ROM and RAM and executes the processes for determining blood pressure according to a program stored in the ROM. This CPU 29 has the functions of extracting DC and pulse wave components from the DC component and the pulse wave component of the cuff pressure signal supplied thereto by way of the A/D converter 28, separating the extracted pulse wave component into a positive component pulse wave and a negative component pulse wave in comparison with a certain reference value, smoothing the separated two component pulse waves individually by moving averaging, combining the smoothed pulse wave components into pulse wave information, and determining average blood pressure, maximum blood pressure, and minimum blood pressure from the cuff pressure signal and the pulse wave information. The determined blood pressure values are displayed on a display unit 30. The CPU 29 is further equipped with the functions of controlling the drive and deactivation of the pressurization pump 24 according to a signal a, and switching the exhaust valve 23 between gradual air exhaustion and rapid air exhaustion by a signal b.

Now, the action of the present embodiment of the electronic blood pressure meter will be described in the following with reference to the flow charts for the program obeyed by the CPU 29 shown in FIGS. 17 and 18.

As the program action starts, first of all, the pressurization pump 24 is driven by the signal "a" and the pressurization of the cuff 21 begins. And this pressurization continues until a cuff pressure which is sufficient for measurement has been built up (by the repetitive decision made in the step ST1). When the cuff pressure reaches a certain predetermined cuff pressure, the drive of the pressurization pump 24 is stopped and the pressurization ends (in the step ST2). And the exhaust valve 23 exhausts the air from the cuff 21 gradually by the signal "b" (in the step ST3) and thereafter the process of measuring the blood pressure begins. Specifically, in the step ST4, the computation of the smoothed value of the pulse wave is performed. This process includes a series of the steps executed from the extraction of the pulse wave component shown in FIG. 15a to the obtaining of the pulse wave information shown in FIG. 15f, and their detailed descriptions will be given hereinafter.

The computation of the smoothed pulse wave information in the step ST4 is performed in time sequence, and it is determined whether the maximum value of the pulse wave information has been determined or not (in the step ST5). The determination result is NO until the maximum value is detected, and in such a case the process of the step ST4 is repeated. When the maximum value of the pulse wave information is detected, the determination result of the the step ST5 becomes YES, and subsequently it is determined whether the value of a variable FLAG is unity or not (in the step ST6). This FLAG is a flag for determining whether the average blood pressure and the maximum blood pressure have already been determined or not, and becomes unity once the average blood pressure and the maximum blood pressure have been determined. Therefore, the determination result of the the step ST6 is initially NO, and after the program flow has advanced to the step ST7 the determination of the average blood pressure and the maximum blood pressure is made. Specifically, in this second preferred embodiment of the present invention, the cuff pressure at which the smoothed value of the pulse wave is the maximum value is determined as the average blood pressure, while the cuff pressure at which the smoothed value of the pulse wave is 50% of the maximum value in the region in which the cuff pressure is higher than the average blood pressure is determined as the maximum blood pressure. And then the value of the variable FLAG is set to unity (in the step ST8). Subsequently, it is determined whether the smoothed value of the pulse wave has become equal to or less than 70% of the maximum value or not (in the step ST9). If it is not equal to or less than 70%, the system flow returns to the step ST4, and the processes following the step ST4 are executed, but since the maximum value of the smoothed value of the pulse wave has been detected and the value of the variable FLAG is unity, the step ST7 and the step ST8 are skipped when they are next reached. When the smoothed value of the pulse wave reaches 70% of the maximum value, then the determination result of the step ST9 becomes YES, and the cuff pressure at which the smoothed value of the pulse wave becomes 75% of the maximum value is determined as the minimum blood pressure in the step ST10. Then, the determined average blood pressure, the maximum blood pressure, and the minimum blood pressure are displayed on the display unit 30 (in the step ST11), and the exhaust valve 23 rapidly exhausts air by the signal "b" before completing the measurement process.

Now, specific processes for computing the smoothed value of the pulse wave in the step ST4 will be described in the following.

Figure 17:
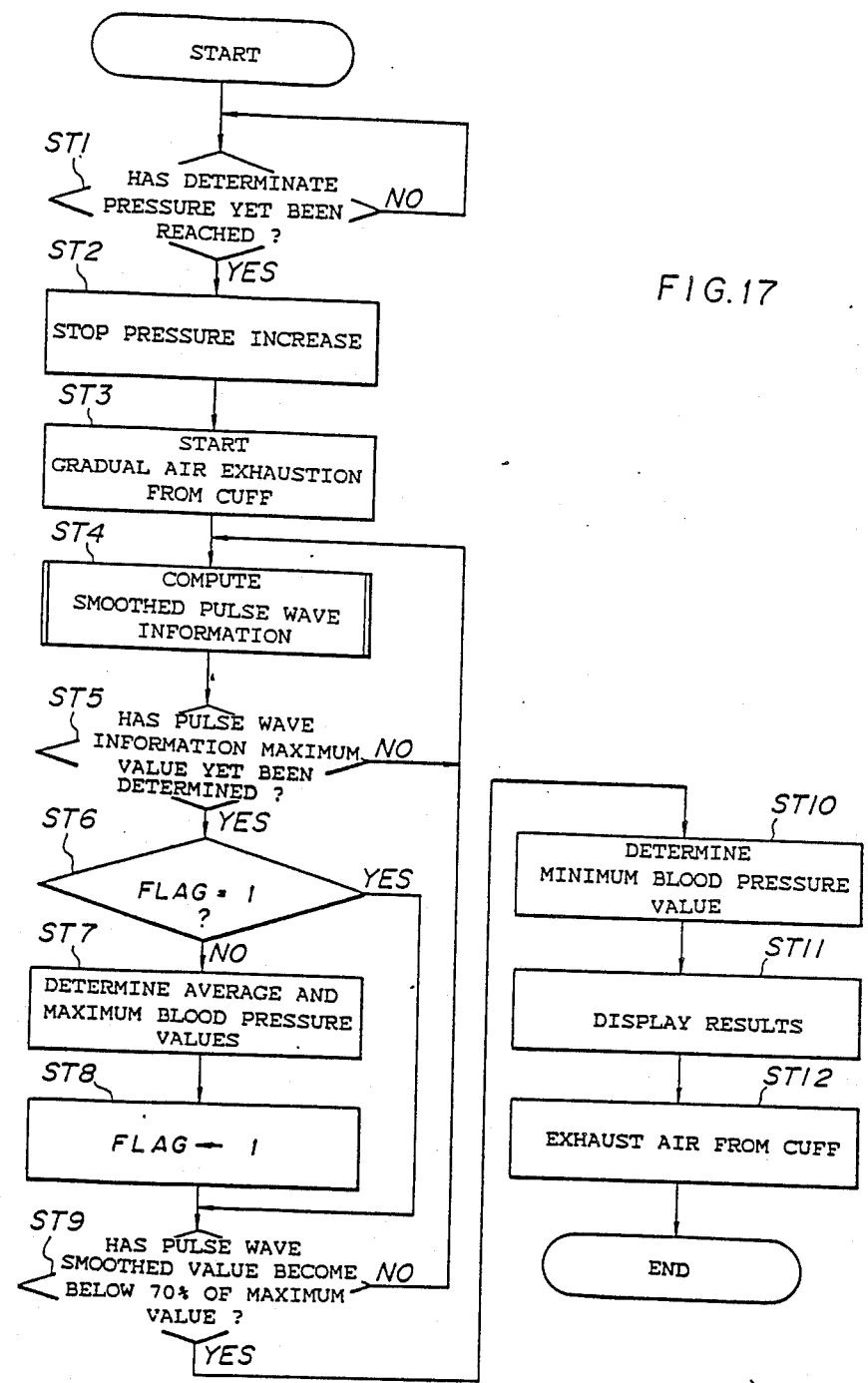
FIG. 17 is a main flow chart for illustrating the action of a program for a microcomputer incorporated in said second preferred embodiment of the electronic blood pressure meter according to the present invention.
Figure 18:
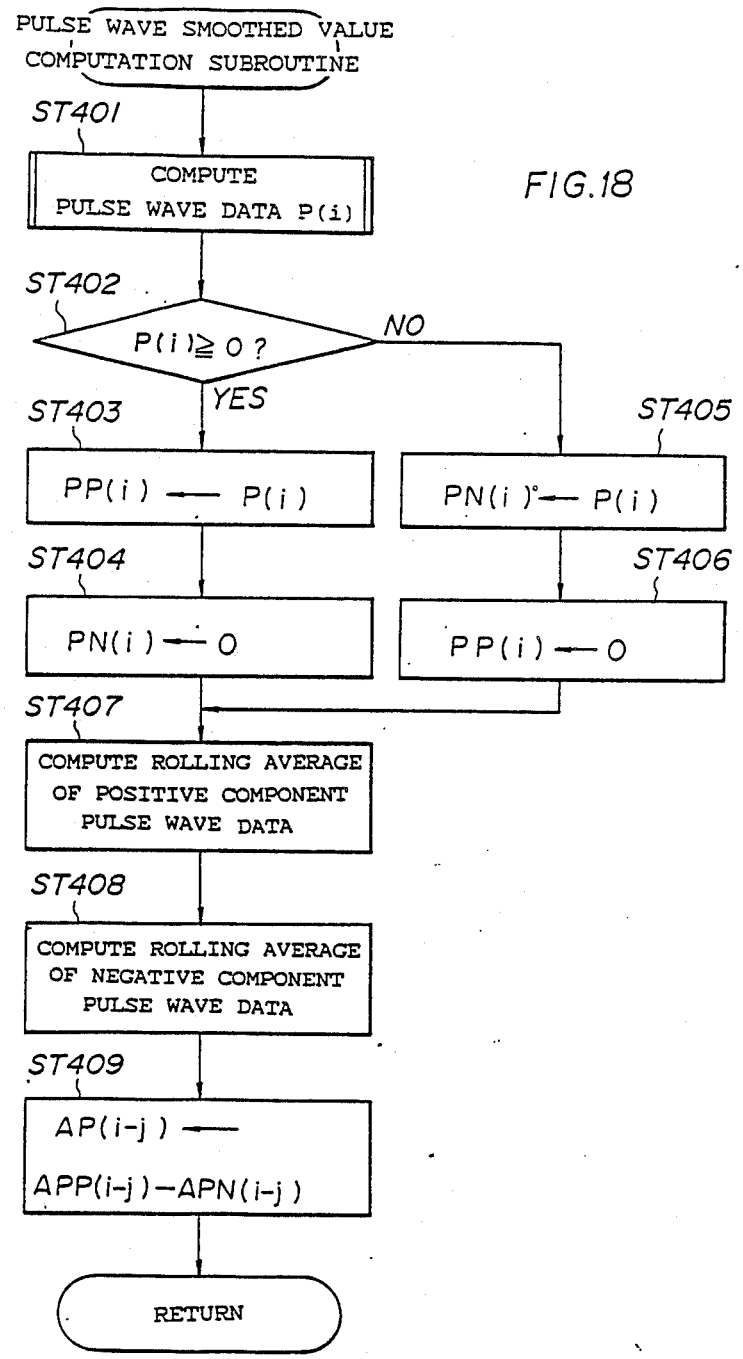
FIG. 18 is a flow chart showing in greater detail a computation routine for a smoothed pulse wave which is called from the main flow chart of FIG. 17.

In the main program flow shown in FIG. 17 and described hereinabove, as the process in the step ST4 begins, first of all the pulse wave data P(i) is computed as shown in FIG. 18 (in the step ST401). The computation of this pulse wave data P(i) in the CPU 29 is performed by a sampling cycle which is performed at intervals of the order of 100 ms for instance. The wave form of this pulse wave data P(i) from the beginning to the end of the measurement is exemplarily shown in FIG. 15a. Next, it is determined whether the pulse wave data P(i) is greater than the reference value L (which is zero in this case) or not (in the step ST402). If P(i) is greater than zero, P(i) is stored as the positive component pulse wave data Pp(i), and zero is stored as the negative component pulse wave data Pn(i) (in the step ST403 and the step ST404). If P(i) is on the other hand determined to be smaller than the reference value L (which is zero in this case) in the step ST402, P(i) is stored as the negative component pulse wave data Pn(i), and zero is stored as the positive component pulse wave data Pp(i) (in the step ST404 and in the step ST405). The wave forms of the positive component pulse wave data Pp(i) and the negative component pulse wave data Pn(i) from the beginning to the end of the measurement are exemplarily shown in FIGS. 15b and 15c.

After the separation of the positive component pulse wave data Pp(i) and the negative component pulse wave data Pn(i) as performed as detailed above from the step ST402 to the step ST406, the computation of the rolling average of the positive component pulse wave App(i) is performed in the step ST407, and then in the step ST408 the rolling average of the negative component pulse wave Apn(i) is performed. These rolling averages App(i) and Apn(i) are computed according to the following equations:

$$APP(i - j) = \frac{PP(i - 2j) + PP(i - 2j + 1) + PP(i - 2j + 2) + \ldots + PP(i - 1) + PP(i)}{2j}$$

$$APN(i - j) = \frac{PN(i - 2j) + PN(i - 2j + 1) + PN(i - 2j + 2) + \ldots + PN(i - 1) + PN(i)}{2j}$$

The wave forms of the rolling average of the positive component pulse wave App(i) and of the rolling average of the negative component pulse wave Apn(i) from the beginning to the end of the measurement are exemplarily shown in FIGS. 15d and 15e.

(f) a pulse wave maximum amplitude extraction means for extracting the maximum value of the wave amplitude from said pulse wave amplitude extraction means;

(g) an area computing means for computing the areas between an envelope line of a certain number of data, including representative data which is extracted in said time sequence by said pulse wave amplitude extraction means, and a line connecting the terminal end data of said data in a sequential manner while shifting the representative data;

(h) a first maximum area value extracting means for finding the maximum value of the area computed on the higher cuff pressure side than the cuff pressure corresponding to the maximum value of the amplitude of the pulse wave;

(i) a second maximum area value extracting means for finding the maximum value of the area computed on the lower cuff pressure side than the cuff pressure corresponding to the maximum value of the amplitude of the pulse wave; and (j) a blood pressure determining means for determining a maximum blood pressure from the cuff pressure corresponding to the maximum area extracted by said first maximum area value extracting means, and a minimum blood pressure from the cuff pressure corresponding to the maximum area extracted by said second maximum area value extracting means.

2. An electronic blood pressure meter as in claim 1 wherein said pulse wave amplitude extraction means is a band pass filter.

3. An electronic blood pressure meter as in claim 1 wherein said pulse wave maximum amplitude extraction means, said area computing means, said first maximum area value extracting means, said second maximum area value extracting means and said blood pressure determining means is a computer processing unit.

* * * * *

Then, the calculation and assignment $$AP(i-j) \leftarrow APP(i-j) - APN(i-j)$$

are performed (in the step ST409), and the sum of the smoothed value of the positive component pulse wave App(i−j) and the smoothed value of the negative component pulse wave Apn(i−j) is set to be the smoothed pulse wave value Ap(i−j). Upon completion of these processes, the flow of control returns to the main program. When the process in step ST4 is repeated until the end of the measurement, a smoothed pulse wave value as exemplarily shown in FIG. 15f is obtained.

Figure 19:
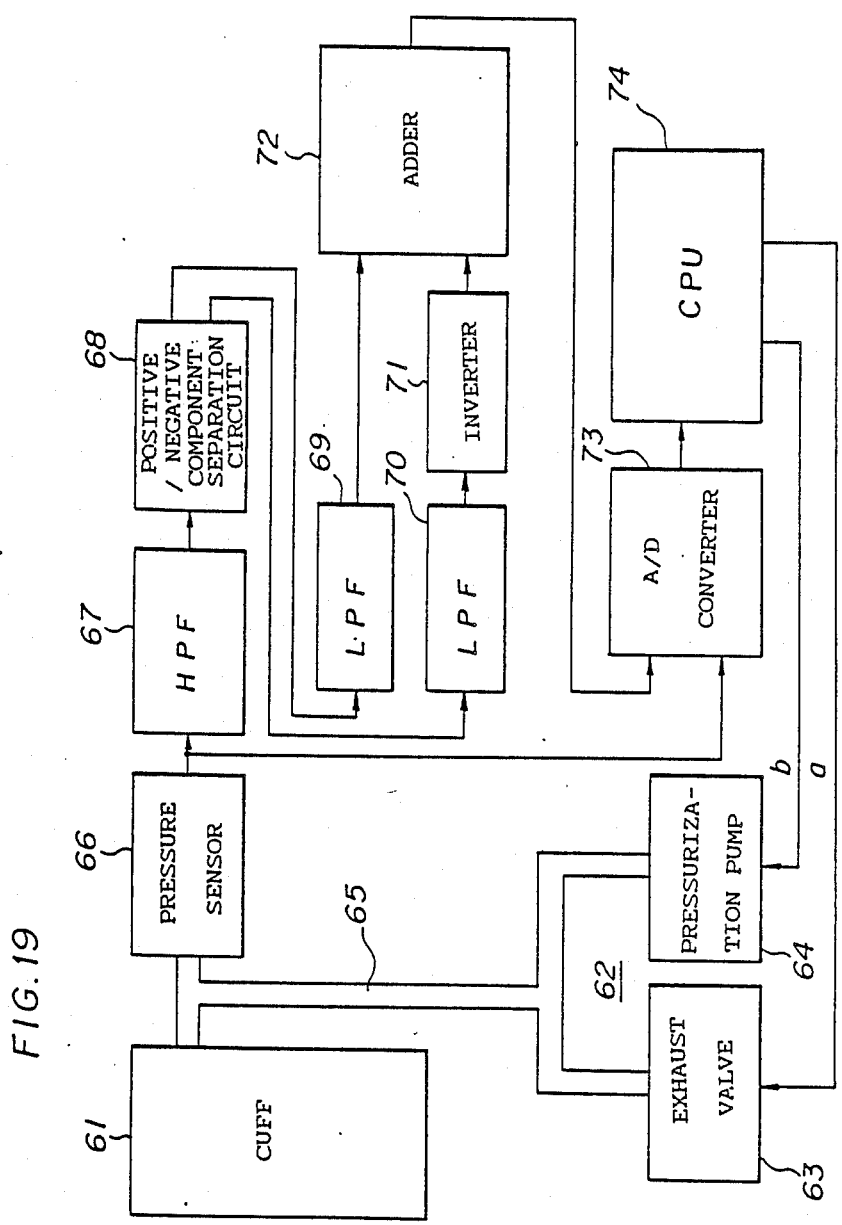
FIG. 19 is a block diagram showing a third preferred embodiment of the electronic blood pressure meter according to the present invention, which utilizes a special electronic circuit for calculation of said smoothed pulse wave, rather than a microcomputer.

Although in the above described second preferred embodiment of the electronic blood pressure meter of the present invention the program flow of the CPU was utilized for obtaining the pulse wave smoothed value, it is also possible as an alternative to use electronic circuitry to obtain pulse wave smoothed values. FIG. 19 is a circuit block diagram of an electronic blood pressure meter which is a third preferred embodiment of the electronic blood pressure meter of the present invention in which the pulse wave smoothed value is obtained by an electronic circuit.

In this drawing, the cuff 61, the pressure system 62, the exhaust valve 63, the pressurization pump 64, the rubber tube 65, and the pressure sensor 66 utilized are similar to those shown in the second preferred embodiment shown in FIG. 16. However, the pressure signal which comprises a pulse wave component overlaid in the cuff pressure which is converted into an electric signal by the pressure sensor 66 is fed to a high pass filter 67, and only the pulse wave component is outputted from said high pass filter 67. The pulse wave component outputted from this high pass filter 67 is supplied to a positive/negative component separation circuit 68, and the pulse wave component is separated into a positive component pulse wave and a negative component pulse wave as exemplarily shown in FIGS. 15b and 15c. These positive and negative component pulse waves are individually supplied to low pass filters 69 and 70, respectively, and after being smoothed by these low pass filters 69 and 70 pulse wave smoothed signals for the positive and the negative components as exemplarily shown in FIGS. 15d and 15e are outputted. And the negative pulse wave smoothed signal is inverted by an inverter 71 and the positive smoothed signal from the low pass filter 69 is added thereto by an adder 72. Therefore, the adder 72 produces a pulse wave smoothed signal in which the positive and the negative pulse wave smoothed signals are combined, as exemplarily shown in FIG. 15f. And this pulse wave smoothed signal is converted into a digital value by an A/D converter 73 before it is supplied to the CPU 74, and the output of the pressure sensor 66 is also converted into a digital signal by the A/D converter 73 as the cuff pressure signal before it is supplied to the CPU 74.

Figure 20:
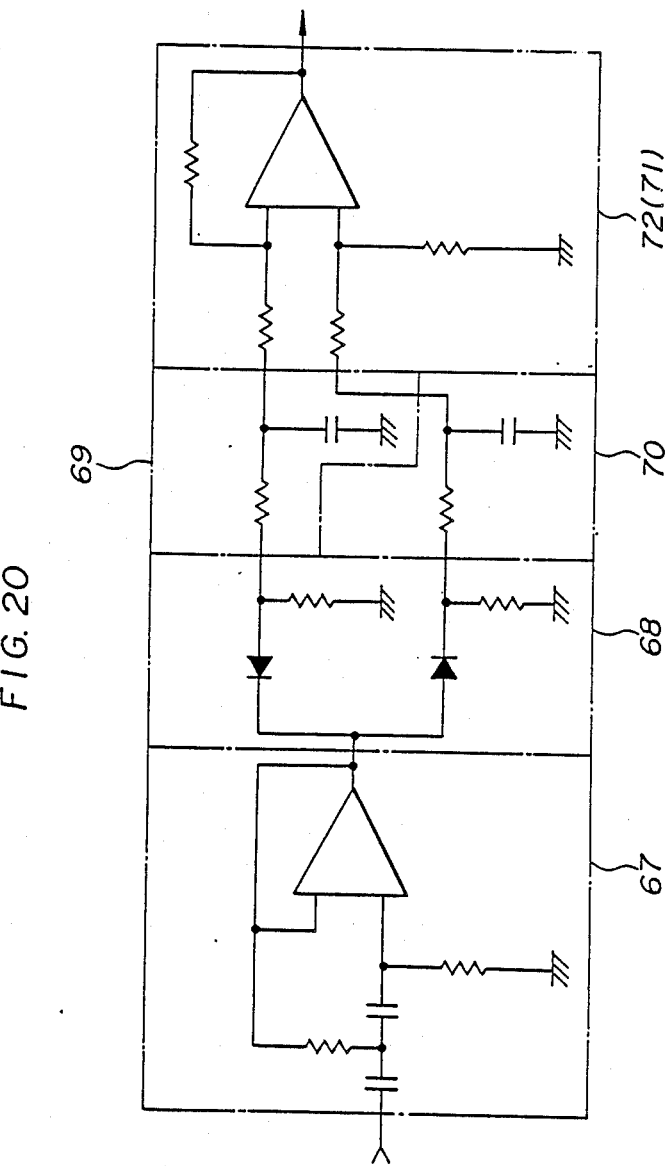
FIG. 20 is a circuit diagram showing a specific construction for a part, only shown in FIG. 19 as a block, of said third preferred embodiment of the electronic blood pressure meter according to the present invention.

Specific circuits for the high pass filter 67, for the positive/negative component separation circuit 68, for the low pass filters 69 and 70, for the inversion circuit 71, and for the adder 72, may be as shown in FIG. 20 for instance. This circuit will be easily understood by one of ordinary skill in the relevant art without undue experimentation, based upon the disclosure herein; accordingly, detailed description thereof will be foregone in the interests of brevity and conciseness of explanation.

The measuring action of this electronic blood pressure meter is executed under the control of the CPU 74, and the computation of the pulse wave smoothed value in the step ST4 of FIG. 17 is performed by the above described electronic circuit, but otherwise the determination of the blood pressure is performed by the CPU 17 in a manner analogous to that performed for the second preferred embodiment of the present invention, as shown by the flow chart of FIG. 17.

According to this third preferred embodiment type of electronic blood pressure meter in which the pulse wave smoothed value is obtained by an electronic circuit, since such an analog circuit for this purpose can be made of relatively simple circuitry, and therefore the processing burden on the CPU can be reduced, therefore a CPU of relatively small memory capacity can be used, and this helps to reduce the cost of the blood pressure meter as a whole.

According to these second and third preferred embodiments of the electronic blood pressure meter of the present invention, since the pulse wave does not need to be recognized for each pulse beat and no complex computation is necessary, development of difficult control programs is not necessary and the memory capacity of the CPU utilized may be small, thereby providing an economical electronic blood pressure meter.

Since a smoothed pulse wave is used, there will be less interference even when the patient happens to have an irregular pulse or he or she moves his or her arm during measurement. Furthermore, since the division of the pulse wave for obtaining an envelope line is not necessary, therefore such an electronic blood pressure meter can be applied to the measurement of the blood pressure of people who have relatively weak pulses.

Furthermore, since Korotkoff sound is not used, this device is not affected by various external noises and other interference, and it can be used for the measurement of the blood pressure of infants and of patients who are in a state of shock. Further, the fact that a Korotkoff sound sensor is not necessary helps to reduce the cost of the electronic blood pressure meter as a whole.

Although the present invention has been shown and described in terms of certain preferred embodiments thereof, and with reference to the appended drawings, it should not be considered as being particularly limited thereby. The details of any particular embodiment, or of the drawings, could be varied without, in many cases, departing from the ambit of the present invention. Accordingly, the scope of the present invention is to be considered as being delimited, not by any particular perhaps entirely fortuitous details of the disclosed preferred embodiments, or of the drawings, but solely by the legitimate and properly interpreted scope of the accompanying claims, which follow.

What is claimed is:

1. an electronic blood pressure meter, comprising:
   (a) a cuff;
   (b) a pressure system coupled to said cuff for pressurizing and evacuating said cuff;
   (c) a pressure sensor coupled to said cuff for detecting the pressure within said cuff;
   (d) a pulse wave sensor coupled to said pressure sensor for detecting the pulse wave component in the course of cuff pressure changes;
   (e) a pulse wave amplitude extraction means, said pulse wave extraction means receiving the output from said pressure sensor and extracting the pulse wave amplitude in time sequence;